United States Patent [19]

Meijer

[11] Patent Number: 4,920,336

[45] Date of Patent: Apr. 24, 1990

[54] METHOD AND APPARATUS FOR MONITORING THE LEVEL OF THE CONTENTS IN A CONTAINER

[75] Inventor: Robert S. Meijer, San Diego, Calif.

[73] Assignee: Fisher Scientific Company, Pittsburgh, Pa.

[21] Appl. No.: 275,323

[22] Filed: Nov. 22, 1988

[51] Int. Cl.⁵ ............................................. G01F 23/00
[52] U.S. Cl. ................................... 340/619; 250/577; 73/293
[58] Field of Search .................. 340/619, 612, 618; 73/293; 250/577

[56] References Cited

U.S. PATENT DOCUMENTS

| | | | |
|---|---|---|---|
| 4,297,588 | 10/1981 | Hastbacka | 73/293 |
| 4,306,525 | 12/1981 | Faxvog | 73/293 |
| 4,631,529 | 12/1986 | Zeitz | 340/619 |
| 4,703,314 | 10/1987 | Spani | 340/619 |
| 4,788,444 | 11/1988 | Williams | 340/619 |

FOREIGN PATENT DOCUMENTS

| | | | |
|---|---|---|---|
| 605108 | 4/1978 | U.S.S.R. | 73/293 |
| 605109 | 4/1978 | U.S.S.R. | 73/293 |

*Primary Examiner*—Hezron E. Williams
*Attorney, Agent, or Firm*—Nydegger & Harshman

[57] ABSTRACT

A method and apparatus are disclosed for monitoring the contents of a container in order to detect when the contents are below a predetermined level. An optical metering signal from a light source driven by a multivibrator is projected at a predetermined level across the space within the container. A light sensor on the opposite side of the space within the container detects incident illumination there. The metering signal is incident there only when the contents of the container are below the predetermined level. Otherwise, the contents either block or refract the metering signal from its normal path, and the metering signal goes undetected. A unity gain amplifier of variable sign coupled to the light sensor and to the multivibrator determines when signal from the light sensor are synchronized with the output of the multivibrator, so as to be deemed to correspond to pulses of the metering signal. Thereupon a status signal is generated by the inventive monitor indicating that the level of the contents of the container is below the predetermined level. The specific embodiment disclosed has particular application to use with a transparent-walled container, such as the drip chamber of a disposable, sterile fluid administration kit.

43 Claims, 4 Drawing Sheets

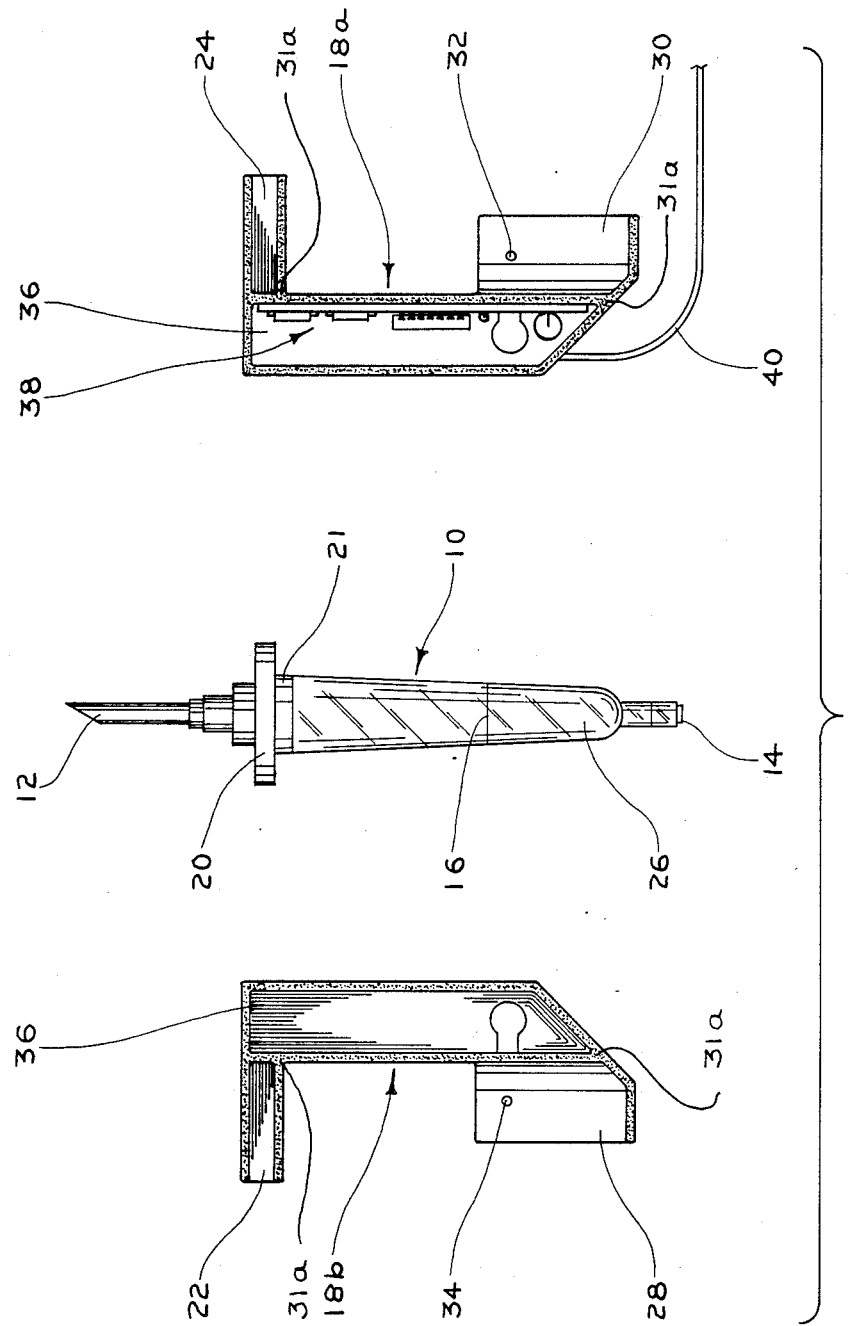

METHOD AND APPARATUS FOR MONITORING THE LEVEL OF THE CONTENTS IN A CONTAINER

BACKGROUND OF THE INVENTION

1. Field of the Invention

This invention relates to monitors for the contents of containers and more particularly to such monitors which detect when the contents of a container are below some predetermined level. The invention has particular applicability to monitoring the level of fluid in reservoirs used to progressively administer solutions to hospital patients.

2. Background Art

Parenteral and enteral solutions are routinely administered to hospital patients through sterile administration sets, which are frequently disposable. Normally, the administration set is removed from its sterile package and connected to a sterile reservoir of the fluid through a spike or cannula that is part of the administration set. The administration set is then filled for priming purposes with the fluid, and a second cannula is used to effect actual connection between the primed administration set and the patient.

As the administration of fluid proceeds, the sterile reservoir becomes progressively depleted. If the reservoir is allowed to go completely empty, continued flow of the fluid will either partially or completely deplete the fluid remaining in the administration set itself.

The presence of any air in the tubing below the drip chamber can not only be a major inconvenience, it can also be a potential hazard to the patient. Once air gets into the tubing leading from a drip chamber to a patient, it effectively precludes continued use of the administration set for the delivery of fluids. Indeed, if this air is not purged from the tubing of the administration set prior to an attempt to administer additional fluid, any fluid subsequently added to the drip chamber or the fluid reservoir thereabove will force an air bolus into the patient. As a practical matter, air in the tubing set can only be removed by either injecting a saline solution into the administration set below the fluid level, or by disconnecting the administration set from the patient and repeating the priming procedures. Either option disrupts the administration of fluids to the patient and increases the risk of inducing bacterial infection.

Various types of mechanical floats, electronic drop detectors, and ultrasonic level detectors exist for the purpose of monitoring the contents of a container, such as the drip chamber in an administration set. As presently implemented, however, each has significant drawbacks.

Mechanical floats are generally disposed to operate a valve located internally to the administration set. The valve is generally in its open position in the presence of a fluid and in its closed position in the absence thereof. Common forms of mechanical floats include a floating disk or a floating ball that occludes an exit port when the level of fluid in the chamber in which the valve has been installed drops sufficiently. Nevertheless, when used as components of a disposable administration set, such devices add significantly to the cost involved.

Accordingly, several monitors have been developed that operate externally to an administration set and that can therefore be reused, saving substantial costs. Among these are electronic devices which can be generally subclassified as optical detectors or ultrasonic detectors.

Several examples can be given of optical devices that operate in conjunction with a drip chamber in an administration set. Typically, such detectors are positioned externally to the administration set to achieve an interruption or deflection of a fixed light beam by drops of fluid falling through a space between one or more light sources and light detectors. The absence at expected intervals of signals responsive to such falling drops is used to indicate the depletion of the fluid in a sterile reservoir.

Optical drop detectors require complex devices to define what time interval between drops constitutes an accepted interval. Further, the optical devices are frequently sensitive to ambient light levels and will often generate erroneous signals due to momentary changes in these levels. In addition, these types of detectors are susceptible to misreadings due to fog forming on the interior wall of the drip chamber which can either obscure the beam of light or trigger false signals through drops of condensed fluid vapor meandering down the drip chamber wall.

In a slightly different operation from the optical detector, ultrasonic fluid level detectors generally utilize the fluid present in the lower half of the drip chamber as a conduit for an ultrasonic signal from a sending transducer. The failure of a receiving transducer to detect the ultrasonic signal which is normally transmitted when fluid fills the lower half of the drip chamber is taken as an indication that fluid has been depleted in the region of the drip chamber which was previously used as a conduit for the ultrasonic beam. Proper coupling of the ultrasonic unit to the administration set requires that both the sending and receiving transducers of the ultrasonic unit be in intimate contact with the walls of the drip chamber. Unfortunately, any significant variation in drip chamber dimensions of different administration sets can obviate this required intimate contact. In addition, the high cost of generating, coupling, receiving, and detecting ultrasonic beams can be major drawbacks in the cost effectiveness of ultrasonic devices.

In light of the above, an object of the present invention is to provide an improved monitor for the contents of a container which will detect when the contents are below a predetermined level.

Another object of the present invention is to provide a monitor as described above which is used externally to the container being monitored, so that the monitor may be reused with successive disposable containers.

Still another object of the present invention is a monitor for the contents of a container which does not depend for its successful operation on measuring the rate of dripping of the fluid from that container. Thus, both generally and in the specific instance mentioned, it is an object of the present invention to eliminate the need to determine and adjust the monitor to any predetermined rate of material or fluid flow in order to monitor the level thereof.

An additional object of the present invention is to produce a monitor as described above that does not require an intimate fit with the exterior of the container in which contents are to be monitored and thus is operable with containers having differing dimensions.

Yet another object of the present invention is to provide a monitor as described above which is not susceptible to erroneous functioning due to light ambient conditions.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

SUMMARY OF THE INVENTION

A monitor, in accordance with the invention as embodied and broadly described herein, for detecting when the contents in a space within a container are below some predetermined level comprises an emitting means and a receiving means. The emitting means produces a modulated optical signal. This signal is produced on a first side of the space outside the container and is directed into the container. In the specific embodiment disclosed herein, the emitter circuit comprises a multivibrator for producing alternating ON and OFF signals and a light source electronically coupled thereto for emitting light responsive to the ON signals.

The receiving means of the novel monitor of the present invention is a phototransistor which generates an electronic signal proportional to illumination incident on a second side of the space outside the container opposite the first side. The optical signal is incident on the second side only when the contents of the container are below the predetermined level. Contents in the container above the predetermined level will either block or optically refract the metering signal from being incident on the receiving means.

The novel monitor also comprises a detection means coupled electrically to the emitting means and to the receiving means for determining when the electronic signal from the receiving means is synchronized with the metering signal, thus to determine when electronic signals from the receiving means correspond to electrical signals stimulated by the reception of an optical metering signal. The detection means may comprise a linear operational amplifier having positive and negative input terminals and an output terminal. The input terminals are connected to other circuit elements so as to result in a unity gain amplifier of variable sign. Specifically, the positive input terminal is coupled to the multivibrator, while the negative input terminal is coupled to the output terminal and both the negative and positive input terminals are coupled to the receiving means.

Additionally, the monitor of the present invention comprises an alerting means responsive to the detection means for generating a status signal when an electronic signal from the receiving means is synchronized with the metering signal from the emitter means. Such a status signal indicates that the level of the contents of the container is below the predetermined level. A suitable alerting means may comprise a voltage divider and a linear operational amplifier having positive and negative input terminals. The positive input terminal is coupled to the voltage divider, while the negative input terminal is coupled to the detection means for receiving an output signal therefrom.

Optionally, the monitor also comprises first and second filter means. The first filter means is interposed between the receiving means and the detection means for removing low frequency components from the electronic signals generated by The receiving means. On the other hand, the second filter means is interposed between the detection means and the alerting means for removing high frequency components from any output signal from the detection means.

In the specific embodiment of the generalized invention disclosed herein, the container in which contents are monitored is a drip chamber in an intravenous fluid administration set. The drip chamber contemplated has transparent walls. The contents of the drip chamber may be transparent or opaque. Thus, the emitting and receiving means described above are located on either side of the drip chamber in a divergently refracted line-of-sight relationship when the level of the fluid in the drip chamber is below some predetermined level. When fluid is in the drip chamber above the predetermined level, the optical effect of the fluid blocks or convergently refracts the modulated signal, so that it is not incident on the receiving means.

The present invention also encompasses a method for determining when the contents in the space within a container are below a predetermined level. That method comprises generating a modulated beam of light, directing the modulated beam of light at the predetermined level horizontally across the space within the container from a first side thereof, detecting light at a second side of the space within the container opposite the first side, and verifying that light detected at the second side corresponds to light in the modulated beam of light.

BRIEF DESCRIPTION OF THE DRAWINGS

In order that the manner in which the above-recited and other advantages and objects of the invention are obtained, a more particular description of one embodiment of the invention briefly described above will be rendered by reference to a specific embodiment thereof which is illustrated in the appended drawings. Understanding that these drawings depict only a typical specific embodiment of the invention and are not therefore to be considered limiting of its scope, the invention will be described with additional specificity and detail through the use of the accompanying drawings in which:

FIG. 2 is a disassembled elevation view of the drip chamber and the mating edges of the halves of the housing of FIG. 1;

DESCRIPTION OF THE PREFERRED EMBODIMENT

Figure 1:
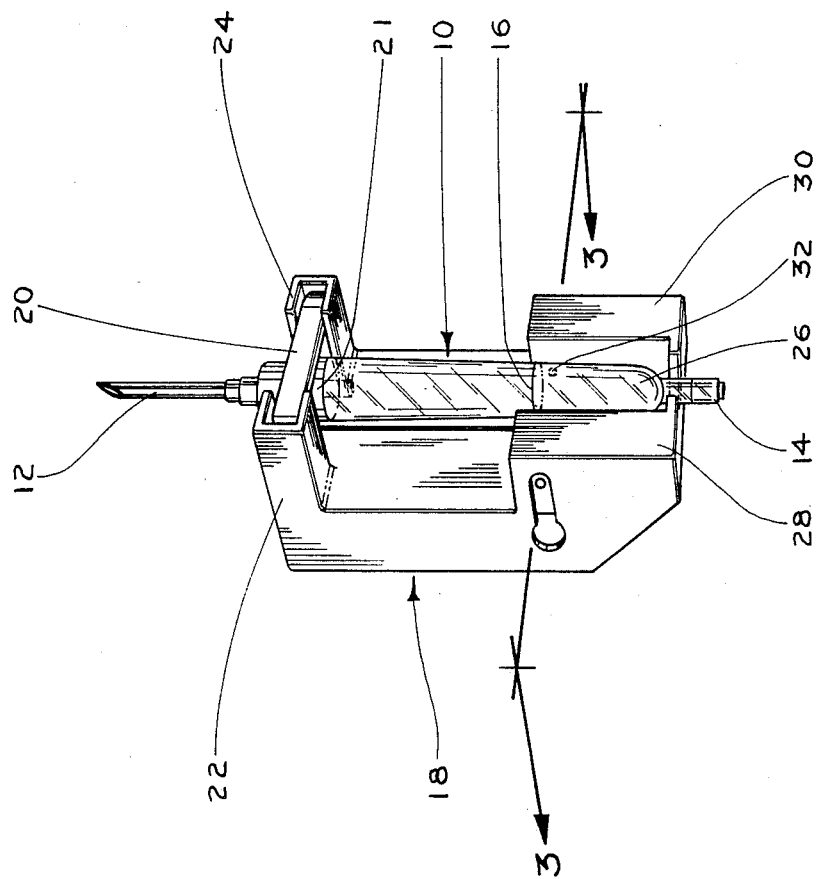
FIG. 1 is a perspective view of a housing for one embodiment of a monitor incorporating the teachings of the present invention, supporting for illustrative purposes the drip chamber of a sterile fluid intravenous administration set.

Shown in FIG. 1 is an example of an embodiment of a monitor configured according to the teachings of the present invention and applied to the specific purpose of detecting when the level of fluid in a transparent-walled container has dropped below a predetermined level. The transparent-walled container is a drop chamber 10, part of a disposable sterile fluid intravenous administration set, not shown. Sterile fluid enters drip chamber 10 from the top thereof through a cannula or spike 12 which in operation is inserted into a reservoir of the sterile fluid through a septum conventionally provided for that purpose. The sterile fluid leaves drip chamber 10 through a connector 14 at the bottom thereof which is linked to the patient receiving the sterile fluid by a second cannula, also not shown. It is the primary function of the embodiment of the present invention described hereafter to detect when the level of sterile fluid in drip chamber 10 is below the predetermined level indicated on the walls of drip chamber 10 by a level marker 16.

All components of the inventive monitor are enclosed within a housing 18 which supports drip chamber 10. This is accomplished by removably receiving a flange 20 at the top 21 thereof between a pair of upper retaining arms 22, 24. The bottom portion 26 of drip chamber 10, including connector 14 is similarly received between a pair of lower retaining arms 28, 30. Significant in monitoring the level of the sterile solution in drip chamber 10 is a first optical portal 32 formed in the side of lower retaining arm 30 adjacent to drip chamber 10. The function of first optical portal 32 will be better understood by reference to FIG. 2.

In FIG. 2 housing 18 can be seen disassembled into a right housing half 18a, which includes upper retainer arm 24 and lower retaining arm 30, and a left housing half 18b which correspondingly includes upper retaining arm 22 and lower retaining arm 28. In FIG. 2 the mating edges 31a and 31b of right and left housing halves 18a and 18b, respectively, are stippled. As has already been described, first optical portal 32 is formed in the side of lower retaining arm 30 adjacent to drip chamber 10 when drip chamber 10 is retained in housing 18. Correspondingly, on the opposite side of chamber 10 from first optical portal 32 a second optical portal 34 is formed in the side of lower retaining arm 28 adjacent to drip chamber 10 when drip chamber 10 is retained in housing 18.

Between upper retaining arms 22, 24 and lower retaining arms 28, 30 right housing half 18a and left housing half 18b are so formed as to together produce a chamber 36 in which are housed the electrical components of the embodiment of the inventive monitor disclosed subsequently. These electronic components are shown by way of illustration including discrete components attached to wiring traces printed on a circuit board 38 that in FIG. 2 is shown resting in the half of chamber 36 formed in right housing half 18a. Power for the electrical components on circuit board 38 is supplied through an electrical cord 40 which exits chamber 36 at the bottom thereof.

Figure 4:
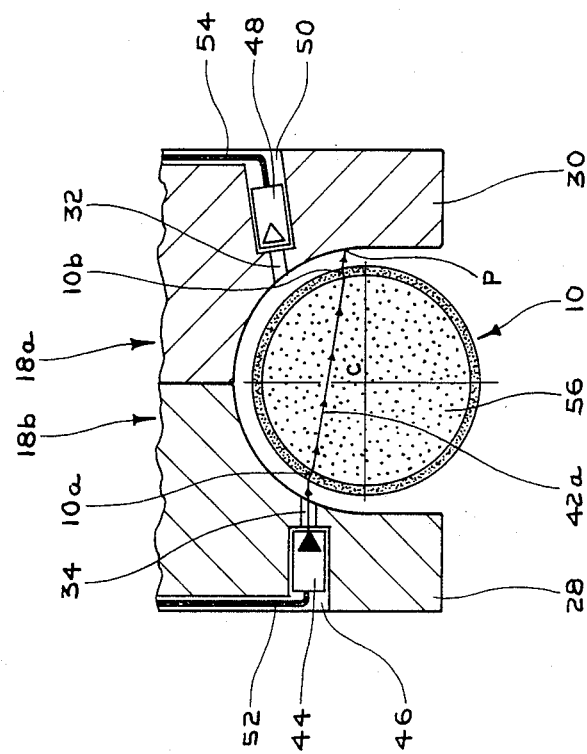
FIG. 4 is a cross-sectional view of the housing and drip chamber shown in FIG. 1 taken along section line 3—3 shown therein, and schematically illustrating the line of travel of an optical metering signal when the level of fluid within the drip chamber is above the level of section line 3—3.
Figure 3:
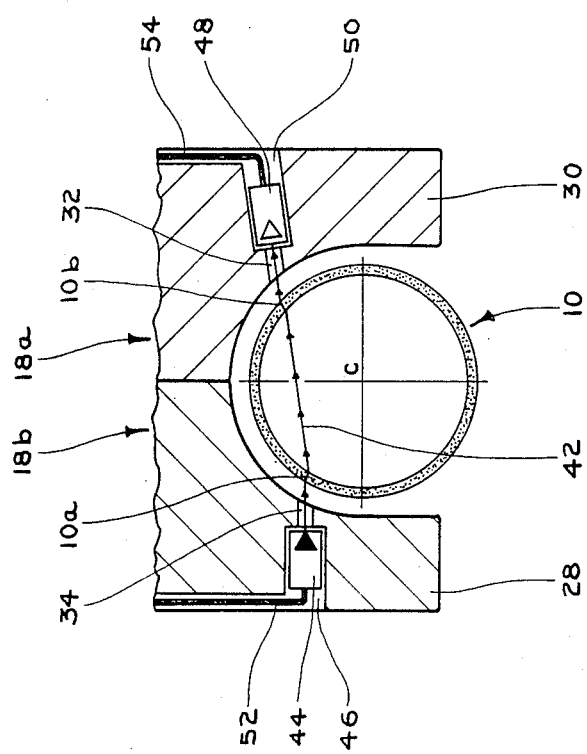
FIG. 3 is a cross-sectional view of the housing and drip chamber shown in FIG. 1 taken along section line 3—3 shown therein, and schematically illustrating the line of travel of an optical metering signal when the level of fluid within the drip chamber is below the level of section line 3—3.

FIGS. 3 and 4, which will be referred to in explaining the optical aspects of the inventive monitor, are cross-sectional views of the housing 18 and drip chamber 10 shown in FIG. 1 taken at the predetermined level indicated therein by level marker 16. As seen in either of these figures, generally cylindrical transparent plastic drip chamber 10 has a lateral cross-section which is circular. In FIG. 3 drip chamber 10 is free of fluid at the level at which the cross-section has been taken. Such an empty drip chamber has the properties of a slightly dispersive lens, that is one with a negative focal length. Thus a ray of light, such as metering signal 42, entering a first wall 10a on a first side of the space within drip chamber 10 and passing through that space and a second wall 10b on a second side of that space will be refracted away from the center C of the cross-section of drip chamber 10.

Thus, for example, in FIG. 3 metering signal 42 is shown as having been produced in a light source 44 housed in a light source chamber communicating with second optical portal 34. After passing through second optical portal 34 and drip chamber 10, metering signal 42 enters first optical portal 32 and is detected by a light sensor 48 within a light sensor chamber 50. Light source 44 and light sensor 48 are connected by electrical leads 52, 54, respectively, with the other circuit components of the inventive monitor, such as those shown in FIG. 2 on circuit board 38. Light source 44 can thus be said to be located on a first side of the space within drip chamber 10, although not being immediately adjacent to that space. A light source such as light source 44 could, for example, be extended through first wall 10a so as to directly contact the contents or space interior thereto. This arrangement, while not shown, is considered to be within the scope of the present invention. Likewise, light sensor 48 can be said to be located on a second side of the space within drip chamber 10 opposite from the first side.

As a result of the optical properties of drip chamber 10 when empty of fluid, light source 44 and light sensor 48 are in a line-of-sight relationship, whereby metering signal 42 from light source 44 reaches light sensor 48 despite passing through drip chamber 10. A different result occurs when drip chamber 10 is filled with a fluid 56 above level marker 16, as shown in FIG. 4. Then, drip chamber 10 behaves like a converging lens, that is one with a positive focal length. Thus, a metering signal 42a enters a wall 10a of drip chamber 1 on a first side of the space therein and passes through fluid 56 to exit drip chamber 10 through a second side 10b located on a second side of the space in drip chamber 10. In the process metering signal 42a is deflected towards the center C of the cross-section of drip chamber 10 in the plane shown, reaching the side of lower retaining arm 30 adjacent to drip chamber 10 at a point P remote from first optical portal 32.

Thus, when sufficient fluid is in drip chamber 10 to fill it above the predetermined level indicated in FIG. 1 by level marker 16, light rays from second optical portal 34 are refracted away from light sensor 48 and not detected. If the fluid in drip chamber 10, or any other transparent-walled container held in housing 18 is opaque, the same result is obtained. When the opaque fluid is above the predetermined level, the passage of light therethrough is either blocked or refracted toward the center of the cross-section of the container and not detected. When the fluid drops below the predetermined level, the optical properties of the container with air therein in combination with the positioning of the light source and light sensor used result in the deflection of light rays as shown in FIG. 3 and their detection by the light sensor.

This then results in the production of a status signal, in a manner to be described subsequently, which indicates that the level of the contents of the chamber is below that predetermined level. In other contexts, it is contemplated that the contents monitored by the present invention may be non-fluid. The same principles of operation would apply as in the case of an opaque fluid.

The manner in which metering signals are produced and, when detected, used to generate a status signal indicating that the level of the contents of the container being monitored is below some predetermined level will be explained by reference to the electrical schematic diagram shown in FIG. 5. First, appropriate levels of power are provided to the circuitry shown by a three-terminal voltage supply comprising a capacitor C2, a resistor R3, and a diode D1. Preferably, diode D1 is a 2.5 volt zener diode of the LM 385-2.5 designation. To these components are provided a high voltage $V_+$ and a low voltage $V_-$ derived from the positive and negative parts, respectively, of a conventional voltage supply. The resulting three-terminal voltage supply produces a ground, a high-level voltage $V_{cc}$, and an intermediate reference common voltage $V_1$.

In accordance with one aspect of the present invention, emitting means are provided for producing an intermittent optical metering signal on a first side of the space within a container the contents of which are being monitored. As shown in FIG. 5, an amplifier D is coupled to a capacitor C4 and resistors R8, R9, R10 so as to function as a multivibrator having a substantially square wave output at a nominal frequency of one kilohertz. These electrical components serve as a switching means for intermittent activation of a light source comprising a light-emitting diode D2, which corresponds to light source 44 shown in FIGS. 3 and 4. Preferably, light-emitting diode D2 has an SE4355-3 designation. Amplifier D, as well as amplifiers A, B, and C located elsewhere within FIG. 5, are each one quarter of a quad amplifier, such as the LM324 marketed by National Semiconductor Corp.

The output terminal of amplifier D is coupled to light-emitting diode D2 through an N-P-N transistor Q3 of the 2N 4401 designation. The collector of transistor Q3 is connected to diode D2, which is in turn coupled to the high reference voltage $V_{cc}$ through a resistor R21. The emitter of transistor Q3 is grounded, while the square wave output of amplifier D is coupled to the base of transistor Q3 through resistor R14. By means of this arrangement, light-emitting diode D2 is sequentially turned on and off in synchronization with the output of amplifier D. Light-emitting diode D2 is thus on when the output of amplifier D is positive and off when that output is negative.

In accordance with another complementary aspect of the present invention, receiving means are provided for generating an electronic signal portional to the illumination on a second side of the space within a container being monitored opposite from the side upon which light-emitting diode D2 is located. As discussed in relation to FIGS. 3 and 4 above, the receiving means is positioned on the second side so that the receiving means detects metering signals from light-emitting diode D2 as part of the illumination there only when the level of the contents in the container is below some predetermined level.

Under most circumstances, the line-of-sight between light-emitting diode D2 and the receiving means is horizontal and at the predetermined level. Nevertheless, the use of a non-horizontal line-of-sight between these elements of the inventive monitor is contemplated as being within the scope of the present invention. In such a case the lowest point in the line-of-sight between light-emitting diode D2, for example, and the receiving means that is interior to drip chamber 10 will necessarily be at that predetermined level. When the contents of drip chamber 10 intersect any part of the line-of-sight between these two elements, light from diode D2 will not be incident upon the receiving means. Once the level of those contents drops below the line-of-sight, light from diode D2 will fall upon the receiving means. If that line-of-sight is not parallel to the top surface of those contents, this will occur when the level of the contents drops below the lowest point on the line-of-sight interior to drip chamber 10.

Figure 5:
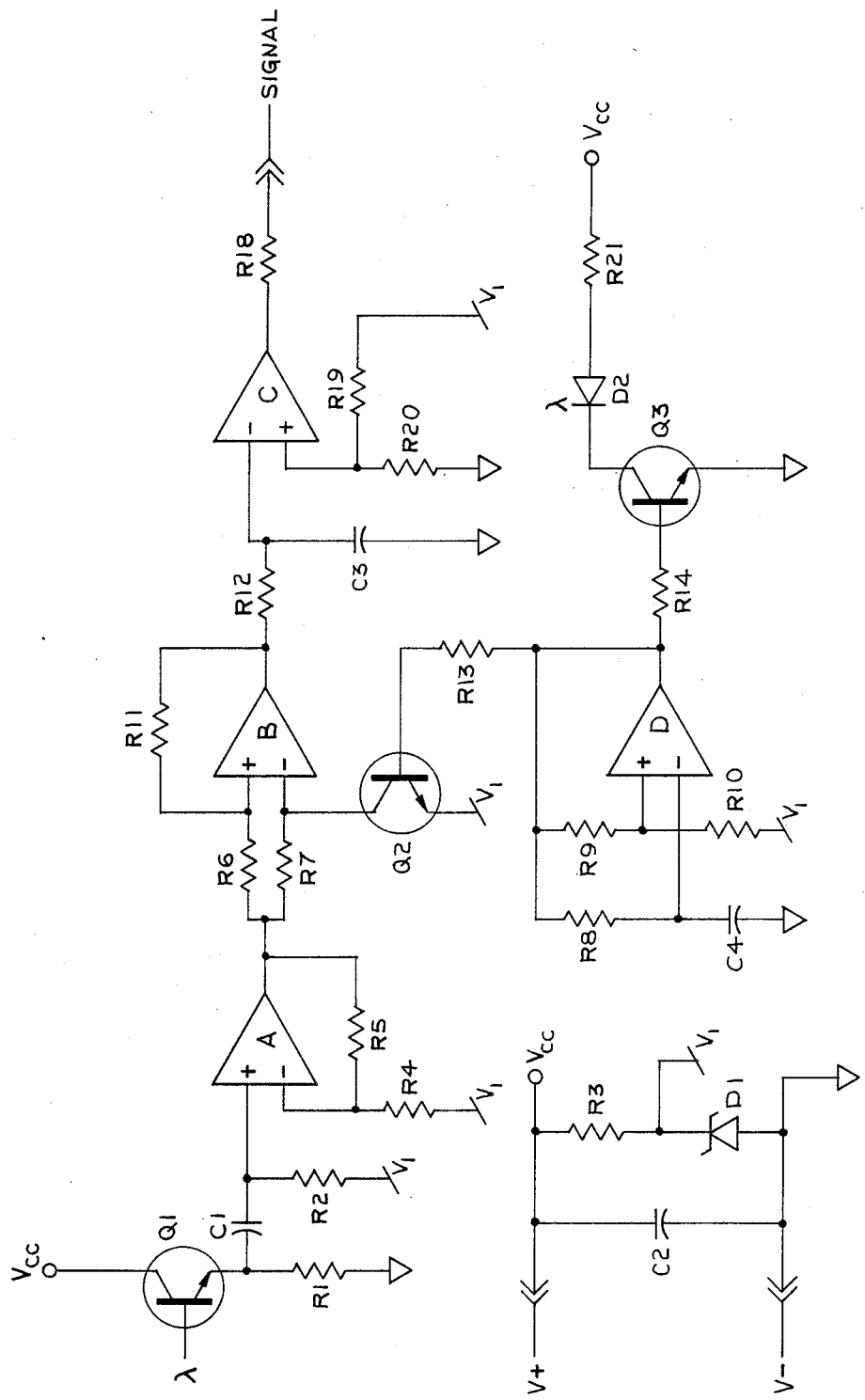
FIG. 5 is a schematic diagram of the electrical components of one embodiment of a monitor according to the teachings of the present invention.

As shown in FIG. 5, a phototransistor Q1 with the collector thereof connected to the high voltage reference $V_{cc}$ and the emitter thereof connected through resistor R1 to ground is responsive to ambient light and light generated by light-emitting diode D2. In the embodiment shown phototransistor Q1 is preferably a darlington pair transistor having an SPX 2532 designation. Phototransistor Q1 is rendered relatively more conductive during the period it receives light, from light-emitting diode Q3 or elsewhere, and relatively less conductive at other times. Photo transistor Q1 thus corresponds to light sensor 48 shown in FIGS. 3 and 4.

It must be emphasized that phototransistor Q1 is responsive to ambient light incident thereupon from any source. The signal at the emitter of phototransistor Q1 is thus a composite signal comprising signals corresponding to the slowly changing ambient light in the environment in which the invention is located and, if incident upon phototransistor Q1, the much more rapidly varying metering signal generated by light-emitting diode D2. For this reason, a first filter means comprising a capacitor C1 and a resistor R2 connected to the reference common voltage $V_1$ are provided for removing low frequency components from the electronic signal generated by phototransistor Q1.

Thus, a signal corresponding substantially to the operation of light-emitting diode D2 is passed to the non-inverting input of an amplifier A connected as shown through resistors R5 and R4 to the reference common voltage $V_1$. Under such circumstance, the output of amplifier A is a square wave of maximum amplitude that is in phase with the output of amplifier D in the multivibrator of the disclosed monitor.

In accordance with yet another aspect of the present invention detection means are provided which are coupled electrically to receive both the amplified form of the signal produced by phototransistor Q1 and the output of amplifier D, which controls light-emitting diode D2. The detection means determines when the electronic signal from phototransistor Q1 is synchronized with the electronic signal controlling light-emitting diode D2 and corresponding to the optical metering signal. As shown by way of example and not limitation, an amplifier B is configured as a unity gain amplifier of variable sign.

Both the positive and the negative input terminals of amplifier B are connected through resistors R7 and R6, respectively, to the output terminal of amplifier A. In addition, the output terminal of amplifier B is connected through a resistor R11 to its own negative input terminal. Finally, the positive input terminal of amplifier B is coupled to the output terminal of amplifier D in the multivibrator. This is accomplished by connecting the gate of a transistor Q2 through a resistor R3 to the output terminal of amplifier D. the emitter of transistor Q2 is connected to the reference common voltage $V_1$, while the collector thereof is connected to the positive input terminal of amplifier B. Preferably, transistor Q2 is an N-P-N transistor having a 2N 4401 designation.

When transistor Q2 is nonconductive, the output of amplifier B is approximately equal to the output of amplifier A. On the other hand, when transistor Q2 is conductive, the output of amplifier B is substantially equal to the negative of the output of amplifier A. Transistor Q2 is, however, only conductive when a signal from amplifier D is causing light-emitting diode D2 to produce a pulse of light in the optical metering signal. If that pulse of light is received by phototransistor Q1, then a corresponding positive signal will appear at the output of amplifier A, and the output of amplifier B will be the negative thereof. The output of amplifier B is thus substantially negative only if the signal derived from phototransistor Q1 is in phase with the operation of transistor Q2 and correspondingly with amplifier D in the multivibrator. Such a negative output signal will be termed hereinafter as a "verification signal." It is only when the electronic signal produced as the output of amplifier A is synchronized with the optical metering signal from diode D2 that such verification signals result.

Amplifier B accordingly verifies that signals generated by phototransistor Q1 are indeed verification signals that accurately reflect the detection of a portion of the optical metering signal from light-emitting diode D2. This is useful in preventing stray electrical signals and electrical signals corresponding to ambient light from being inadvertently taken to indicate that the level of the fluid in the container being monitored is below the predetermined level.

In accordance with yet another aspect of the present invention, a second filter means is provided for removing high frequency components from the output signal of amplifier B. As shown by way of example, and not limitation, a resistor R12 and a capacitor C3 connected in the manner shown serve to integrate out of the signal produced by amplifier B switching transients and the effects, if any, remaining in that signal from ambient light. The combination of resistor R12 and capacitor C3 also serves to minimize the effect of fluid sloshing in the drip chamber or other container being monitored when the support therefore is moved from one location to another.

The monitor of the present invention also includes an alerting means responsive to verification signals from amplifier B for generating a status signal whenever the electronic signal from amplifier A is synchronized with the metering light signal generated by light-emitting diode D2. The status signal thus indicates that the level of the contents of the container being monitored is below some predetermined level at which the metering signal can pass across the space within the container.

As shown by way of example and not limitation, a normative means comprising a resistor R20 and a resistor R19 connected in the manner shown to ground and the reference common voltage $V_1$, respectively, are used to establish a reference signal which is provided to the positive input terminal of an amplifier C.

The negative input terminal of amplifier C is supplied through the second filter means comprising resistor R12 and capacitor C3 with the output from amplifier B.

Thus, amplifier C functions as a comparator means for indicating according to a predetermined relationship between the output signal from amplifier B and the reference signal from resistors R19, R20, that the level of the contents in the container being monitored is below the predetermined level.

The output of amplifier B is negative only when the metering signal from light-emitting diode D2 has been received by phototransistor Q1. When the level of the output of amplifier B is more negative than the reference signal provided to the positive input terminal of amplifier C, a signal appears through resistor R18 at the output of amplifier C indicating that the fluid level in the drip chamber or other container being monitored is insufficient. On the other hand, if the level of the output of amplifier B is substantially equal to zero volts or more positive than the reference signal provided to the positive input of amplifier C, this indicates that an adequate supply of the contents of the container being monitored yet remain therein.

The embodiment of the inventive monitor is specially adapted for use with a reusable sterile fluid infusion kit, generally referred to as an IV administration set. Nevertheless, the broad principles of the invention disclosed encompass the monitoring of contents dry or wet in containers of all types. Where those containers do not as drip chamber 10, have transparent walls, the invention may yet be practices through the provision of appropriately located apertures through which light sources and light sensors may be in visual communication when the contents of the container have dropped below the level of those apertures.

The physical values of the resistive and capacitive components shown in FIG. 5, are listed in the table below. All resistors have 0.25 watt capacities.

TABLE 1

| Component Values in FIG. 1 | |
|---|---|
| C1 = 0.22 μf | C3 = 4.7 μf |
| C2 = 4.7 μf | C4 = 0.047 μf |
| R1 = 470Ω | R12 = 5.6KΩ |
| R2 = 2.2KΩ | R13 = 10KΩ |
| R3 = 1.0KΩ | R14 = 3.3KΩ |
| R4 = 2.2KΩ | R15 = 1.2KΩ |
| R5 = 100KΩ | R16 = 3.3KΩ |
| R6 = 10KΩ | R17 = 3.3KΩ |
| R7 = 10KΩ | R18 = 470Ω |
| R8 = 15KΩ | R19 = 10KΩ |
| R9 = 47KΩ | R20 = 15KΩ |
| R10 = 22KΩ | R21 = 68Ω |
| R11 = 10KΩ | |

The invention disclosed herein also includes a method for determining when the contents in the space within a container are below a predetermined level. That method comprises the steps of generating an intermittent beam of light and directing the intermittent beam of light, usually horizontally at the predetermined level, across the space within the container from a first side thereof. On the second side of the space within the container ambient light is detected on a continuing basis. The intermittent beam of light, however, is detected as light on the second side of the space within the container only when the level of the contents of the container is below the predetermined level. Finally, the method of the present invention involves verifying that any light detected at the second side of the space within the container corresponds in fact to the intermittent beam of light generated. When this occurs a verification signal is generated for comparison with the reference signal. When the verification signal has a predetermined value relative to the reference signal, an attention signal is created which indicates that the level of the contents of the container is below the predetermined level.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A monitor of the contents in a container for detecting when the contents are below a predetermined level, said monitor comprising:
    (a) emitting means on a first side of the container for producing an intermittent optical metering signal directed into the container;
    (b) receiving means on a second side of the container opposite said first side thereof for generating an electronic signal proportional to illumination incident on said receiving means, said optical metering signal being incident to said receiving means only when the contents of the container are below the predetermined level;
    (c) detection means coupled electronically to said emitting means and said receiving means for producing a verification signal when said electronic signal is synchronized with said metering signal; and
    (d) alerting means coupled electronically to said detection means for generating a status signal in response to said verification signal, said status signal indicating that the level of the contents of the container is below the predetermined level.

2. A monitor as recited in claim 1, wherein the contents of the container cause refraction of said optical metering signal when the level of the contents of the container is above the predetermined level.

3. A monitor as recited in claim 1, wherein the contents of the container block said optical metering signal when the level of the contents of the container is above the predetermined level.

4. A monitor as recited in claim 1, wherein the predetermined level is defined by the lowest point inside the container on the line of sight between said emitting means when the contents therein are below the predetermined level.

5. A monitor as recited in claim 4, wherein the predetermined level is defined by said line of sight between said emitting means and said receiving means inside the container when the contents thereof are below the predetermined level.

6. A monitor as recited in claim 1, wherein said emitting means comprises:
    (a) a light source on a first side of the space within the container; and
    (b) switching means for intermittent activation of said light source, said switching means having an output terminal coupled to said light source and producing at said output terminal an intermittent control signal for activation of said light source.

7. A monitor as recited in claim 1, wherein said emitting means comprises:
    (a) a multivibrator for producing alternating ON and OFF signals; and
    (b) a light source electronically coupled to said multivibrator for emitting light responsive to said ON signal, said light source being located on a first side of the space within the container and being oriented such that light emitted thereby is directed into the container.

8. A monitor as recited in claim 7, wherein said light source comprises a light-emitting diode.

9. A monitor as recited in claim 1, wherein said receiving means comprises a light-sensitive semiconductor device.

10. A monitor as recited in claim 9, wherein said light-sensitive semiconductor device comprises a phototransistor.

11. A monitor as recited in claim 1, further comprising first filter means interposed between said receiving means and said detection means for removing low frequency components from said electronic signal generated by said receiving means.

12. A monitor as recited in claim 1, wherein said detection means comprises a unity gain amplifier of variable sign.

13. A monitor as recited in claim 1, wherein said verification signal is a negative signal.

14. A monitor as recited in claim 6, wherein said detection means comprises a linear operational amplifier having positive and negative input terminals and an output terminal, said positive input terminal being coupled to said output terminal of said switching means, said negative input terminal being coupled to said output terminal, and said negative and said positive input terminals being coupled to said receiving means.

15. A monitor as recited in claim 1, wherein said alerting means comprises:
    (a) normative means for establishing a reference signal; and
    (b) comparator means electronically coupled to said detection means and to said normative means for indicating according to a predetermined relationship between an output signal from said detection means and said reference signal that said output signal corresponds to said verification signal.

16. A monitor as recited in claim 1, wherein said alerting means comprises:
    (a) a linear operational amplifier having a positive and negative input terminal, said negative input terminal being coupled to said detection means for receiving an output signal therefrom; and
    (b) a voltage divider coupled to said positive input terminal.

17. A monitor as recited in claim 1, further comprising second filter means interposed between said detection means and said alerting means for removing low frequency components from an output signal from said detection means.

18. A monitor as recited in claim 1, further comprising a three-terminal voltage supply source.

19. A monitor of the contents in a container for detecting when the contents are below a predetermined level, said monitor comprising:
    (a) a multivibrator for providing at an output terminal thereof alternating ON and OFF signals;
    (b) a light source electronically coupled to said output terminal of said multivibrator for emitting light responsive to said ON signal, said light source being located on a first side of the space within the container and being oriented such that light emitted thereby is directed into the container;
(c) a light sensor located on a second side of the space within the container opposite the first side thereof for generating an electronic signal proportional to illumination incident on said light sensor, said optical metering signal being incident to said light sensor only when the contents of the container are below the predetermined level;
(d) a detector electronically coupled to said light sensor and said multivibrator for producing as an output signal a verification signal when said electronic signal is synchronous with said ON signal, said verification signal being negative and indicating that the level of the contents in the container is below the predetermined level.

20. A monitor as recited in claim 19, further comprising:
(a) normative means for establishing a reference signal; and
(b) comparator means electronically coupled to said detector and to said normative means for indicating according to a predetermined relationship between an output signal from said detector and said reference signal that said output signal corresponds to said verification signal.

21. A monitor as recited in claim 19, wherein said light source comprises a light-emitting diode.

22. A monitor as recited in claim 19, wherein said light sensor comprises a light-sensitive semiconductor device.

23. A monitor as recited in claim 22, wherein said light-sensitive semiconductor device comprises a phototransistor.

24. A monitor as recited in claim 19, further comprising first filter means for removing low-frequency components from said electronic signal generated by said light sensor.

25. A monitor as recited in claim 19, wherein said detector comprises a unity gain amplifier of variable sign.

26. A monitor as recited in claim 19, wherein said detector comprises a linear operational amplifier having positive and negative input terminals and an output terminal, said positive input terminal being coupled to said output terminal on said multivibrator, said negative input terminal being coupled to said output terminal, and said negative and positive input terminals being coupled to said light sensor.

27. A monitor as recited in claim 19, further comprising second filter means for removing low-frequency components from an output signal of said detector.

28. A monitor as recited in claim 19, further comprising a three-terminal voltage supply.

29. A monitor as recited in claim 19, said light source and said light sensor are positioned to establish a line-of-sight therebetween which is horizontal.

30. A monitor of the contents in a clear-walled container for detecting when the contents are below a predetermined level, said monitor comprising:
(a) a light source on a first side of the container;
(b) switching means for activating said light source;
(c) a light sensor on a second side of the container opposite the first side thereof for generating an electronic signal responsive to illumination incident on said light sensor, light from said light source being incident on said light sensor only when the level of the contents of the container is below the predetermined level;
(d) a timing comparator electrically coupled to said switching means and to said light sensor for generating an output signal when said light source is activated simultaneously with the receipt of said electronic signal from said light sensor;
(e) normative means for establishing a reference signal; and
(f) comparator means electronically coupled to said timing comparator and to said normative means for indicating according to a predetermined relationship between an output signal from said timing comparator and said reference signal that light from said light source is incident on said light sensor.

31. A monitor as recited in claim 30, wherein said switching means comprises a multivibrator.

32. A monitor as recited in claim 30, wherein said optical means comprises a light-emitting diode.

33. A monitor as recited in claim 30, further comprising:
(a) first filter means interposed between said light sensor and said timing comparator for removing low-frequency components from said electronic signal; and
(b) second filter means interposed between said timing comparator and said comparator means for removing low-frequency components from said output signal of said timing comparator.

34. A monitor as recited in claim 30, wherein said timing comparator comprises a unity gain amplifier of variable sign.

35. A monitor as recited in claim 30, wherein said output signal of said timing comparator is negative when said light source is activated simultaneously with the receipt of light therefrom at said light sensor.

36. A monitor as recited in claim 35, wherein said comparator means comprises a linear operational amplifier having positive and negative input terminals and an output terminal, said positive input terminal being coupled to said switching means, said negative input terminal being coupled to said output terminal, and said negative and said positive input terminals being coupled to said detector means.

37. A monitor as recited in claim 30, wherein said normative means comprises a voltage divider.

38. A monitor of the contents in a transparent-walled container for detecting when the contents are below a predetermined level, said monitor comprising:
(a) a multivibrator for providing alternating ON and OFF signals;
(b) a light source electronically coupled to said multivibrator and located on a first side of the container for emitting light on the predetermined level in the direction of the container responsive to said ON signals;
(c) a light-sensitive semiconductor device at the predetermined level on a second side of the container opposite the first side thereof, said semiconductor device generating an electronic signal proportional to illumination incident on said semiconductor device and being positioned so light from said light source is incident on said semiconductor device only when the level of the contents in the container is below the predetermined level;

(d) a first filter means for removing low-frequency components from the electronic signal generated by said semiconductor device;
(e) a unity gain amplifier of variable sign coupled electronically to said multivibrator and to said semiconductor device for generating a negative output signal when said electrónic signal is synchronized with ON signals from said multivibrator;
(f) second filter means for removing low-frequency components from said output signal of said unity gain amplifier;
(g) a voltage divider for establishing a reference signal; and
(h) comparator means electronically coupled to said unity gain amplifier and to said normative means for indicating according to a predetermined relationship between said output signal of said unity gain amplifier and said reference signal that light from said light source is incident on said semiconductor device.

39. A monitor as recited in claim 38, wherein the contents of the container are a transparent fluid, and the presence of the transparent fluid in the container at the predetermined level refracts light from said light source to preclude said light from being incident on said semiconductor device.

40. A method for determining when the contents in a container are below a predetermined level, the method comprising:
(a) generating an intermittent beam of light;
(b) directing said intermittent beam of light at the predetermined level across the space within the container from a first side thereof;
(c) detecting incident illumination at a second side of the space within the container opposite the first side, said intermittent beam being incident illumination at said second side only when the level of the contents of the container is below the predetermined level;
(d) verifying that light detected at said second side corresponds to the intermittent beam of light by generating a verification signal wherein said verification signal is generated when the generation of said intermittent beam of light at said first side is synchronous with the detection thereof at said second side;
(e) generating a reference signal;
(f) comparing said verification signal with said reference signal; and
(g) generating a status signal when said verification signal has a predetermined value relative said reference signal.

41. A method as recited in claim 40, wherein said step of generating comprises intermittently activating a light-emitting diode with a multivibrator.

42. A method as recited in claim 40, wherein the container is transparent and in said step of directing and said step of detecting said intermittent beam of light passes through said first and second sides of the container at the predetermined level.

43. A method as recited in claim 40, wherein the contents of the container are a transparent fluid, and in said step of directing, the presence of the transparent fluid in the container at the predetermined level refracts said intermittent beam of light from being incident illumination at the second side.

* * * * *